US011288591B2

United States Patent
Saha et al.

(10) Patent No.: US 11,288,591 B2
(45) Date of Patent: Mar. 29, 2022

(54) PER-ARTICLE PERSONALIZED MODELS FOR RECOMMENDING CONTENT EMAIL DIGESTS WITH PERSONALIZED CANDIDATE ARTICLE POOLS

(71) Applicant: Microsoft Technology Licensing, LLC, Redmond, WA (US)

(72) Inventors: Ankan Saha, San Francisco, CA (US); Ajith Muralidharan, Sunnyvale, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 771 days.

(21) Appl. No.: 15/442,069

(22) Filed: Feb. 24, 2017

(65) Prior Publication Data

US 2018/0060756 A1 Mar. 1, 2018
US 2019/0213501 A9 Jul. 11, 2019

Related U.S. Application Data

(60) Provisional application No. 62/378,674, filed on Aug. 23, 2016.

(51) Int. Cl.
*G06N 20/00* (2019.01)
*G06Q 50/00* (2012.01)
(Continued)

(52) U.S. Cl.
CPC ........... *G06N 20/00* (2019.01); *G06F 16/248* (2019.01); *G06F 16/2471* (2019.01);
(Continued)

(58) Field of Classification Search
CPC .......... G06N 20/00; G06N 5/022; G06N 5/04; G16H 70/60; G16H 80/00; G16H 10/60;
(Continued)

(56) References Cited

U.S. PATENT DOCUMENTS 9,122,989 B1 * 9/2015 Morris ................... G06Q 30/02
2011/0022602 A1 * 1/2011 Luo ........................ G06Q 10/10
707/748

(Continued)

OTHER PUBLICATIONS

Li, Qing, et al. "User Comments for News Recommendation in Forum-Based Social Media." Information Sciences, Elsevier, Sep. 3, 2010, https://www.sciencedirect.com/science/article/pii/S0020025510004251.*
Lee, Jong-Seok, et al. "Classification-based collaborative filtering using market basket data." Expert systems with applications 29.3 (2005): 700-704. (Year: 2005).*
Park, Seung-Taek, and Wei Chu. "Pairwise preference regression for cold-start recommendation." Proceedings of the third ACM conference on Recommender systems. 2009. (Year: 2009).*

(Continued)

*Primary Examiner* — Li B. Zhen
*Assistant Examiner* — Markus A. Vasquez
(74) *Attorney, Agent, or Firm* — Schwegman Lundberg & Woessner, P.A.

(57) ABSTRACT

A system, a machine-readable storage medium storing instructions, and a computer-implemented method as described herein are directed to a Personalized Article Engine that generates respective prediction models for each article in a plurality of candidate articles in a social network system. The Personalized. Article Engine generates a respective article score according to each article's prediction model and at least one feature of a target member account. The Personalized Article Engine generates a plurality of output scores based on combining each respective article score with a corresponding article's global model score. The Personalized Article Engine ranks the output scores to identify a subset of candidate articles relevant to the target member account.

23 Claims, 7 Drawing Sheets

(51) Int. Cl.
*G06N 5/04* (2006.01)
*G06F 16/248* (2019.01)
*G06F 16/2458* (2019.01)
*G06F 16/25* (2019.01)
*G16H 70/60* (2018.01)
*G06N 5/02* (2006.01)
*H04L 67/306* (2022.01)
*G16H 80/00* (2018.01)
*G16H 10/60* (2018.01)
*H04L 67/10* (2022.01)
*H04L 67/01* (2022.01)

(52) U.S. Cl.
CPC ........... *G06F 16/256* (2019.01); *G06N 5/022* (2013.01); *G06N 5/04* (2013.01); *G06Q 50/01* (2013.01); *G16H 70/60* (2018.01); *G16H 80/00* (2018.01); *H04L 67/306* (2013.01); *G16H 10/60* (2018.01); *H04L 67/10* (2013.01); *H04L 67/42* (2013.01)

(58) Field of Classification Search
CPC .. G06F 16/2471; G06F 16/256; G06F 16/248; G06Q 50/01; H04L 67/306; H04L 67/10; H04L 67/42
See application file for complete search history.

(56) References Cited

U.S. PATENT DOCUMENTS

| | | | |
|---|---|---|---|
| 2011/0258256 A1* | 10/2011 | Huberman | G06F 17/278 709/204 |
| 2012/0023043 A1 | 1/2012 | Cetin et al. | |
| 2012/0259919 A1* | 10/2012 | Yan | G06Q 30/02 709/204 |
| 2013/0073568 A1 | 3/2013 | Federov et al. | |
| 2013/0170541 A1 | 7/2013 | Pace et al. | |
| 2015/0081609 A1* | 3/2015 | Hande | H04L 51/32 706/46 |
| 2015/0242967 A1* | 8/2015 | Shsh | G06Q 50/01 705/319 |
| 2015/0317357 A1* | 11/2015 | Harmsen | G06N 20/00 707/723 |
| 2017/0061286 A1* | 3/2017 | Kumar | G06Q 30/0269 |

OTHER PUBLICATIONS

"Non Final Office Action Issued in U.S. Appl. No. 15/441,967", dated Jun. 1, 2020, 40 Pages.

"Final Office Action Issued in U.S. Appl. No. 15/441,967", dated Dec. 4, 2020, 25 Pages.

* cited by examiner

PER-ARTICLE PERSONALIZED MODELS FOR RECOMMENDING CONTENT EMAIL DIGESTS WITH PERSONALIZED CANDIDATE ARTICLE POOLS

CROSS-REFERENCE TO RELATED APPLICATIONS

This application claims the benefit of priority to U.S. Provisional Patent Application entitled "PER-ARTICLE PERSONALIZED MODELS FOR RECOMMENDING CONTENT EMAIL DIGESTS WITH PERSONALIZED CANDIDATE ARTICLE POOLS", Ser. No. 62/378,674, filed Aug. 23, 2016, which is hereby incorporated herein by reference in its entirety.

This application is related to U.S. Patent Application entitled "PER-ARTICLE PERSONALIZED MODEL FEATURE TRANSFORMATION", U.S. patent application Ser. No. 15/441,967, which is hereby incorporated herein by reference in its entirety.

TECHNICAL FIELD

The subject matter disclosed herein generally relates to the technical field of special-purpose machines that facilitate determining relevance of content, including software-configured computerized variants of such special-purpose machines and improvements to such variants, and to the technologies by which such special-purpose machines become improved compared to other special-purpose machines that facilitate determining relevance of content.

BACKGROUND

A social networking service is a computer- or web-based application that enables users to establish links or connections with persons for the purpose of sharing information with one another. Some social networking services aim to enable friends and family to communicate with one another, while others are specifically directed to business users with a goal of enabling the sharing of business information. For purposes of the present disclosure, the terms "social network" and "social networking service" are used in a broad sense and are meant to encompass services aimed at connecting friends and family (often referred to simply as "social networks"), as well as services that are specifically directed to enabling business people to connect and share business information (also commonly referred to as "social networks" but sometimes referred to as "business networks").

With many social networking services, members are prompted to provide a variety of personal information, which may be displayed in a member's personal web page. Such information is commonly referred to as personal profile information, or simply "profile information", and when shown collectively, it is commonly referred to as a member's profile. For example, with some of the many social networking services in use today, the personal information that is commonly requested and displayed includes a member's age, gender, interests, contact information, home town, address, the name of the member's spouse and/or family members, and so forth. With certain social networking services, such as some business networking services, a member's personal information may include information commonly included in a professional resume or curriculum vitae, such as information about a person's education, employment history, skills, professional organizations, and so on. With some social networking services, a member's profile may be viewable to the public by default, or alternatively, the member may specify that only some portion of the profile is to be public by default. Accordingly, many social networking services serve as a sort of directory of people to be searched and browsed.

DESCRIPTION OF THE DRAWINGS

Some embodiments are illustrated by way of example and not limitation in the figures of the accompanying drawings in which.

DETAILED DESCRIPTION

Figure 1:
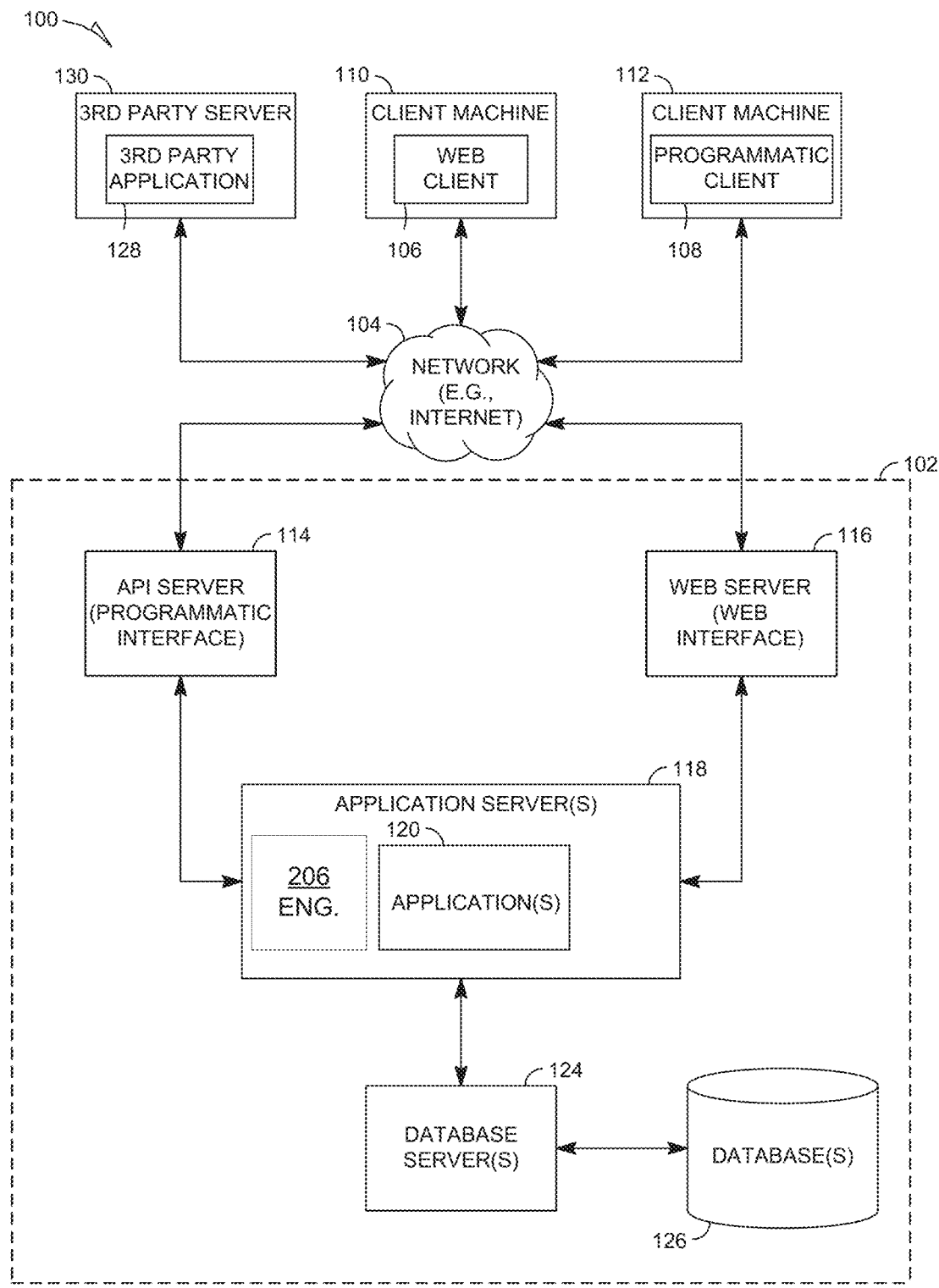
FIG. 1 is a block diagram illustrating a client-server system, in accordance with an example embodiment.

The present disclosure describes methods and systems for determining relevance of content in social network service (also referred to herein as a "professional social network" or "social network"). In the following description, for purposes of explanation, numerous specific details are set forth in order to provide a thorough understanding of the various aspects of different embodiments of the present invention. It will be evident, however, to one skilled in the art, that the present invention may be practiced without all of the specific details.

A system, a machine-readable storage medium storing instructions, and a computer-implemented method as described herein are directed to a Personalized Article Engine that generates respective prediction models for each article in a plurality of candidate articles in a social network system. The Personalized Article Engine generates a respective article score according to each article's prediction model and at least one feature of a target member account. The Personalized Article Engine generates a plurality of output scores based on combining each respective article score with a corresponding article's global model score. The Personalized Article Engine ranks the output scores to identify a subset of candidate articles relevant to the target member account.

The Personalized Article Engine improves the performance of a special-purpose computer system by more efficiently and effectively identifying relevant content in a social network system that may include millions of member accounts and millions of various types of content.

According to exemplary embodiments, the Personalized Article Engine builds and trains a prediction model for each article in a plurality of articles. Each prediction model for an article can be a logistic regression model with features identified by profile data of those member accounts that have interacted with the corresponding article. Each prediction model generates a score for its corresponding article based on a dot product of a regression coefficient vector and a vector based on features of a target member account. For example, a member feature vector is assembled to represent prediction model features present in the target member account and a prediction model vector based on prediction model coefficients that correspond to those present features. A dot product of the member feature vector and the prediction model vector is calculated to generate an output score. The output score can be added to a global model score to determine an overall score for an article.

The global model has a plurality of features and coefficients that can determine relevance of a given article to a target member account. The global model can be a logistic regression model that includes a plurality of member features and a plurality of article features. In the global model, a feature vector is assembled based on present global model features of the target member account and a given article and a global vector is assembled based on global model coefficients that correspond to those present features. A global model score generated by the global model is based on a dot product of the feature vector and the global vector. The global model score represents a generalized score of the given article's relevance to the target member account. Each article is ranked according to its corresponding overall score (i.e. overall output score for an article for a target member account=article's global model score+score calculated by the prediction model that corresponds with the article).

A subset of the ranked articles (such as, for example, the top five articles) are selected for a digest message to be sent to the target member account. The digest message includes a listing of the top five articles and provides access to each of the top five articles. As such, the digest message facilitates engagement and activity of the target member account in the social network service by recommending highly relevant content that would be of interest to the target member account.

According to various embodiments, the global model and each prediction model of the Personalized Article Engine may be executed for the purposes of both off-line training for generating, training, and refining of one or more of the prediction models. According to various embodiments, the Personalized Article Engine builds and trains the global model and a prediction model for each article in a plurality of article. The global model can be a logistic regression model with features based on member account attribute types and article attribute types. Each prediction model for an article can be a logistic regression model with features identified by profile data of those member accounts that have interacted with the corresponding article. Each prediction model generates a score for its corresponding article based on a dot product of a regression coefficient vector and a vector based on features of a target member account.

Various example embodiments further include encoded instructions that comprise operations to generate a user interface(s) and various user interface elements. The user interface and the various user interface elements can be representative of any of the operations, data, prediction models, output, pre-defined features, identified features, coefficients, member accounts, notifications, profile data, articles, one or more type of member account interactions with articles, messages and notifications as described herein. In addition, the user interface and various user interface elements are generated by the Personalized Article Engine for display on a computing device, a server computing device, a mobile computing device, etc.

As described in various embodiments, the Personalized Article Engine may be a configuration-driven system for building, training, and deploying prediction models for determining relevance of articles for a target member account. In particular, the operation of the Personalized Article Engine is completely configurable and customizable by a user through a user-supplied configuration file such as a JavaScript Object Notation (JSON), eXtensible Markup Language (XML) file, etc.

For example, each module in the Personalized Article Engine may have text associated with it in a configuration file(s) that describes how the module is configured, the inputs to the module, the operations to be performed by module on the inputs, the outputs from the module, and so on. Accordingly, the user may rearrange the way these modules are connected together as well as the rules that the various modules use to perform various operations. Thus, whereas conventional prediction modelling is often performed in a fairly ad hoc and code driven manner, the modules of the Personalized Article Engine may be configured in a modular and reusable fashion, to enable more efficient prediction modelling.

Turning to FIG. 1 is a block diagram illustrating a client-server system, in accordance with an example embodiment. A networked system 102 provides server-side functionality via a network 104 (e.g., the Internet or Wide Area Network (WAN)) to one or more clients. FIG. 1 illustrates, for example, a web client 106 (e.g., a browser) and a programmatic client 108 executing on respective client machines 110 and 112.

An Application Program Interface (API) server 114 and a web server 116 are coupled to, and provide programmatic and web interfaces respectively to, one or more application servers 118. The application servers 118 host one or more applications 120. The application servers 118 are, in turn, shown to be coupled to one or more database servers 124 that facilitate access to one or more databases 126. While the applications 120 are shown in FIG. 1 to form part of the networked system 102, it will be appreciated that, in alternative embodiments, the applications 120 may form part of a service that is separate and distinct from the networked system 102.

Further, while the system 100 shown in FIG. 1 employs a client-server architecture, the present disclosure is of course not limited to such an architecture, and could equally well find application in a distributed, or peer-to-peer, architecture system, for example. The various applications 120 could also be implemented as standalone software programs, which do not necessarily have networking capabilities.

The web client 106 accesses the various applications 120 via the web interface supported by the web server 116. Similarly, the programmatic client 108 accesses the various services and functions provided by the applications 120 via the programmatic interface provided by the API server 114.

FIG. 1 also illustrates a third party application 128, executing on a third party server machine 130, as having programmatic access to the networked system 102 via the programmatic interface provided by the API server 114. For example, the third party application 128 may, utilizing information retrieved from the networked system 102, support one or more features or functions on a website hosted by the third party. The third party website may, for example, provide one or more functions that are supported by the relevant applications of the networked system 102. In some embodiments, the networked system 102 may comprise functional components of a professional social network.

Figure 2:
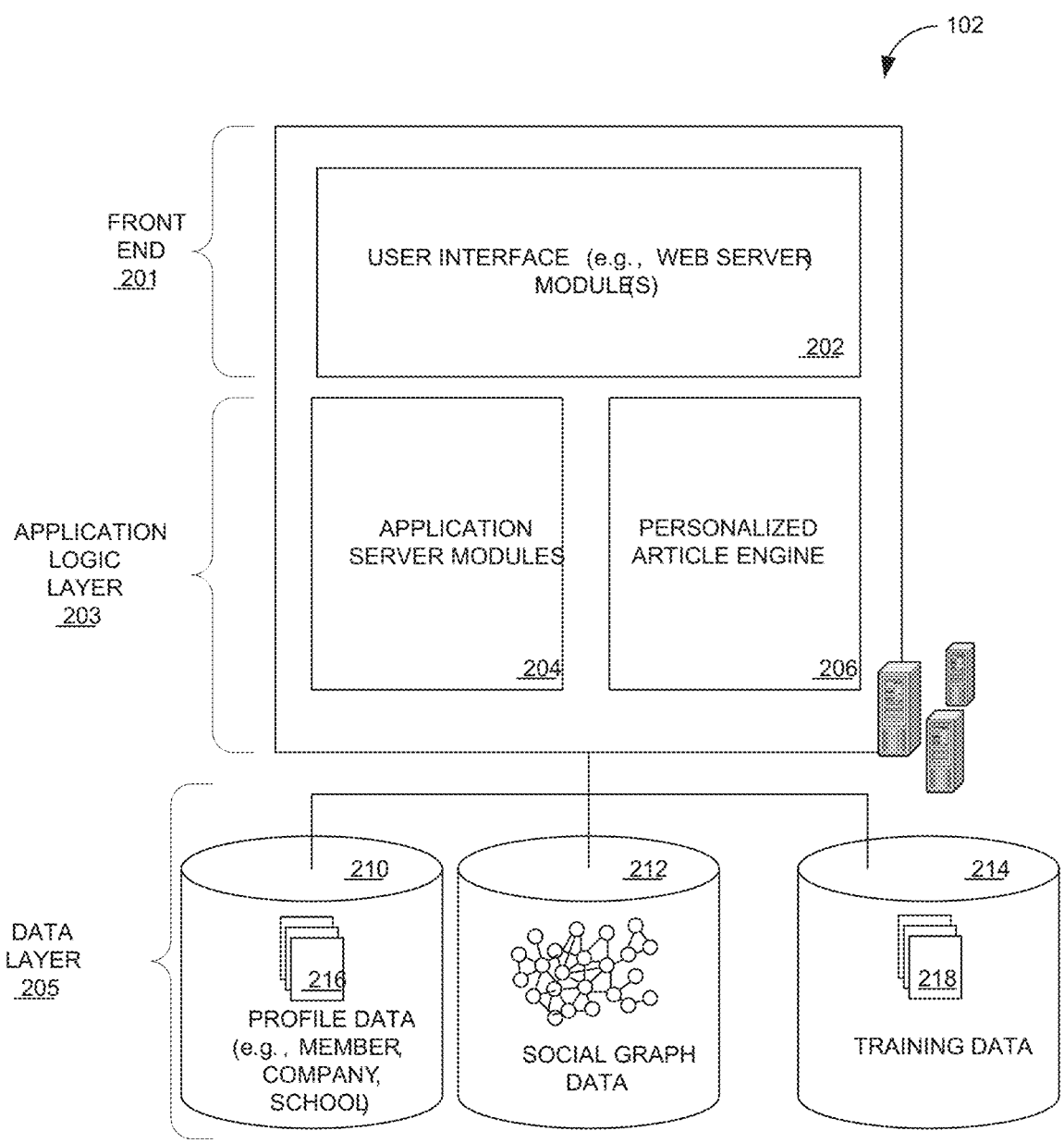
FIG. 2 is a block diagram showing functional components of a professional social network within a networked system, in accordance with an example embodiment.

FIG. 2 is a block diagram showing functional components of a professional social network within the networked system 102, in accordance with an example embodiment.

As shown in FIG. 2, the professional social network may be based on a three-tiered architecture, consisting of a front-end layer 201, an application logic layer 203, and a data layer 205. In some embodiments, the modules, systems, and/or engines shown in FIG. 2 represent a set of executable software instructions and the corresponding hardware (e.g., memory and processor) for executing the instructions. To avoid obscuring the inventive subject matter with unnecessary detail, various functional modules and engines that are not germane to conveying an understanding of the inventive subject matter have been omitted from FIG. 2. However, one skilled in the art will readily recognize that various additional functional modules and engines may be used with a professional social network, such as that illustrated in FIG. 2. to facilitate additional functionality that is not specifically described herein. Furthermore, the various functional modules and engines depicted in FIG. 2 may reside on a single server computer, or may be distributed across several server computers in various arrangements. Moreover, although a professional social network is depicted in FIG. 2 as a three-tiered architecture, the inventive subject matter is by no means limited to such architecture. It is contemplated that other types of architecture are within the scope of the present disclosure.

As shown in FIG. 2, in some embodiments, the front-end layer 201 comprises a user interface module (e.g., a web server) 202, which receives requests and inputs from various client-computing devices, and communicates appropriate responses to the requesting client devices. For example, the user interface module(s) 202 may receive requests in the form of Hypertext Transport Protocol (HTTP) requests, or other web-based, application programming interface (API) requests.

In some embodiments, the application logic layer 203 includes various application server modules 204, which, in conjunction with the user interface module(s) 202, generates various user interfaces (e.g., web pages) with data retrieved from various data sources in the data layer 205. In some embodiments, individual application server modules 204 are used to implement the functionality associated with various services and features of the professional social network. For instance, the ability of an organization to establish a presence in a social graph of the social network service, including the ability to establish a customized web page on behalf of an organization, and to publish messages or status updates on behalf of an organization, may be services implemented in independent application server modules 204. Similarly, a variety of other applications or services that are made available to members of the social network service may be embodied in their own application server modules 204.

As shown in FIG. 2, the data layer 205 may include several databases, such as a database 210 for storing profile data 216, including both member profile attribute data as well as profile attribute data for various organizations. Consistent with some embodiments, when a person initially registers to become a member of the professional social network, the person will be prompted to provide some profile attribute data such as, such as his or her name, age (e.g., birthdate), gender, interests, contact information, home town, address, the names of the member's spouse and/or family members, educational background (e.g., schools, majors, matriculation and/or graduation dates, etc.), employment history, skills, professional organizations, and so on. This information may be stored, for example, in the database 210. Similarly, when a representative of an organization initially registers the organization with the professional social network the representative may be prompted to provide certain information about the organization. This information may be stored, for example, in the database 210, or another database (not shown). With some embodiments, the profile data 216 may be processed (e.g., in the background or offline) to generate various derived profile data. For example, if a member has provided information about various job titles the member has held with the same company or different companies, and for how long, this information can be used to infer or derive a member profile attribute indicating the member's overall seniority level, or a seniority level within a particular company. With some embodiments, importing or otherwise accessing data from one or more externally hosted data sources may enhance profile data 216 for both members and organizations. For instance, with companies in particular, financial data may be imported from one or more external data sources, and made part of a company's profile.

The profile data 216 may also include information regarding settings for members of the professional social network. These settings may comprise various categories, including, but not limited to, privacy and communications. Each category may have its own set of settings that a member may control.

Once registered, a member may invite other members, or be invited by other members, to connect via the professional social network. A "connection" may require a bi-lateral agreement by the members, such that both members acknowledge the establishment of the connection. Similarly, with some embodiments, a member may elect to "follow" another member. In contrast to establishing a connection, the concept of "following" another member typically is a unilateral operation, and at least with some embodiments, does not require acknowledgement or approval by the member that is being followed. When one member follows another, the member who is following may receive status updates or other messages published by the member being followed, or relating to various activities undertaken by the member being followed. Similarly, when a member follows an organization, the member becomes eligible to receive messages or status updates published on behalf of the organization. For instance, messages or status updates published on behalf of an organization that a member is following will appear in the member's personalized data feed or content stream. In any case, the various associations and relationships that the members establish with other members, or with other entities and objects, may be stored and maintained as social graph data within a social graph database 212.

The professional social network may provide a broad range of other applications and services that allow members the opportunity to share and receive information, often customized to the interests of the member. For example, with some embodiments, the professional social network may include a photo sharing application that allows members to upload and share photos with other members. With some embodiments, members may be able to self-organize into groups, or interest groups, organized around a subject matter or topic of interest. With some embodiments, the professional social network may host various job listings providing details of job openings with various organizations.

In some embodiments, the professional social network provides an application programming interface (API) module via which third-party applications can access various services and data provided by the professional social network. For example, using an API, a third-party application may provide a user interface and logic that enables an authorized representative of an organization to publish messages from a third-party application to a content hosting platform of the professional social network that facilitates presentation of activity or content streams maintained and presented by the professional social network. Such third-party applications may be browser-based applications, or may be operating system-specific. In particular, some third-party applications may reside and execute on one or more mobile devices (e.g., a smartphone, or tablet computing devices) having a mobile operating system.

The data in the data layer 205 may be accessed, used, and adjusted by a Personalized Article Engine 206 as will be described in more detail below in conjunction with FIGS. 3-7. Although the Personalized Article Engine 206 is referred to herein as being used in the context of a professional social network, it is contemplated that it may also be employed in the context of any website or online services, including, but not limited to, content sharing sites (e.g., photo- or video-sharing sites) and any other online services that allow users to have a profile and present themselves or content to other users. Additionally, although features of the present disclosure are referred to herein as being used or presented in the context of a web page, it is contemplated that any user interface view (e.g., a user interface on a mobile device or on desktop software) is within the scope of the present disclosure.

The data layer 205 further includes a database 214 that includes training data 214 for generating one or more prediction models. Such training data 214 can be, for example, identifiers of one or more member account that have interacted with an article(s). The database 214 can further store one or more prediction models.

Figure 3:
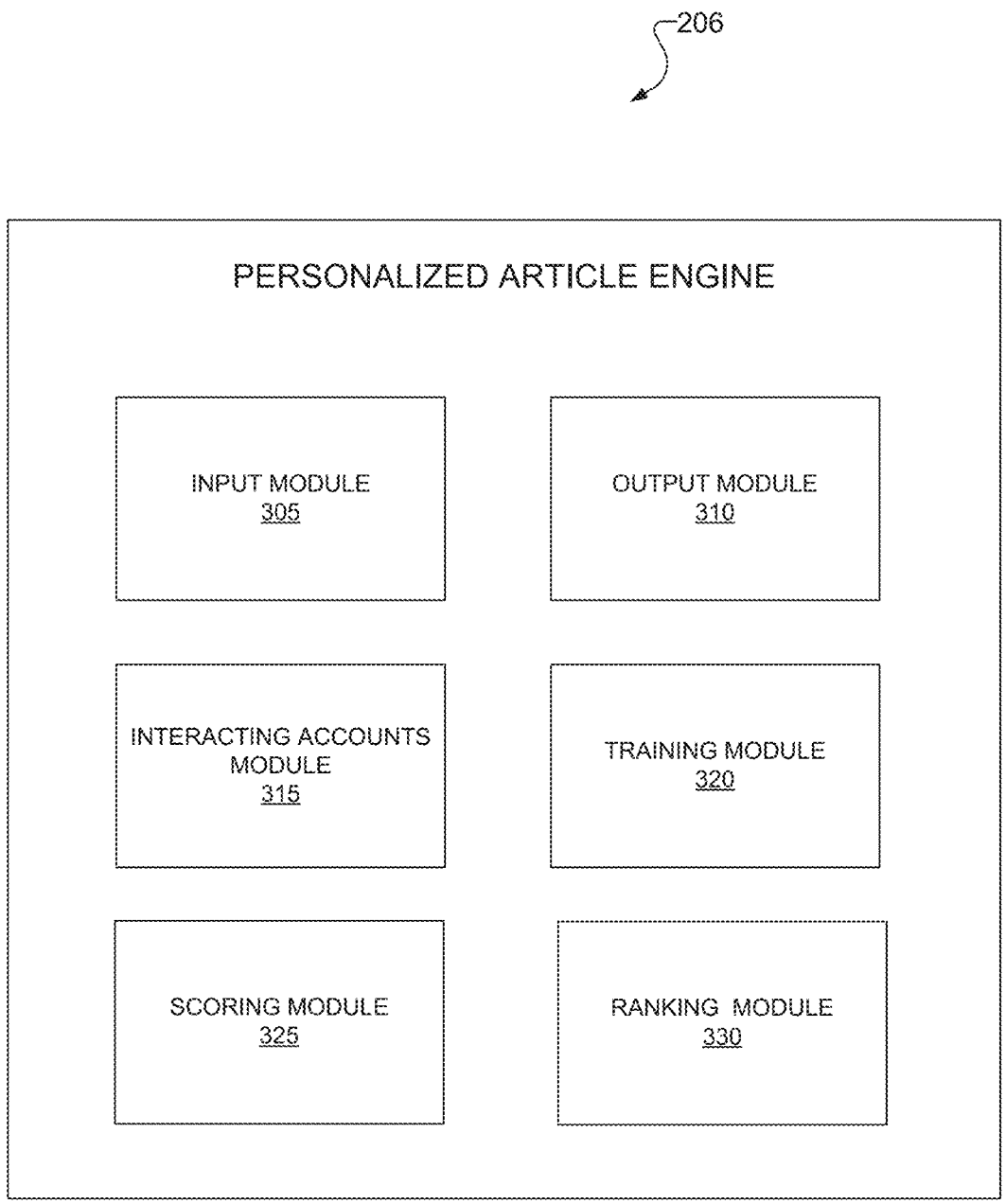
FIG. 3 is a block diagram showing example components of a Personalized Article Engine, according to some embodiments.

FIG. 3 is a block diagram showing example components of a Personalized Article Engine, according to some embodiments.

The input module 305 is a hardware-implemented module that controls, manages and stores information related to any inputs from one or more components of system 102 as illustrated in FIG. 1 and FIG. 2. In various embodiments, the inputs include, in part, one or more candidate articles, profile data of member accounts that have interacted with the one or more candidate articles and profile data of a target member account.

The output module 310 is a hardware-implemented module that controls, manages and stores information related to which sends any outputs to one or more components of system 100 of FIG. 1 (e.g., one or more client devices 110, 112, third party server 130, etc.). In some embodiments, the output is a message or notification that includes a digest (such as a listing) of one or more articles that have scores that indicate a relevance to the target member account.

The interacting account module 315 is a hardware implemented module which manages, controls, stores, and accesses information related to collecting identifications and profile data of each member account that accesses each article in a plurality of candidate articles.

The training module 320 is a hardware-implemented module which manages, controls, stores, and accesses information related to generating a prediction model for each article in a plurality of candidate articles.

The scoring module 325 is a hardware-implemented module which manages, controls, stores, and accesses information related to calculating a score based on vectors assembled according to encoded instructions of a prediction model.

The ranking module 330 is a hardware-implemented module which manages, controls, stores, and accesses information related to ranking scores produced as output from each prediction model for each article. It is understood that a module can be a software module, such as a set of instructions executable on one or more hardware processors.

Figure 4:
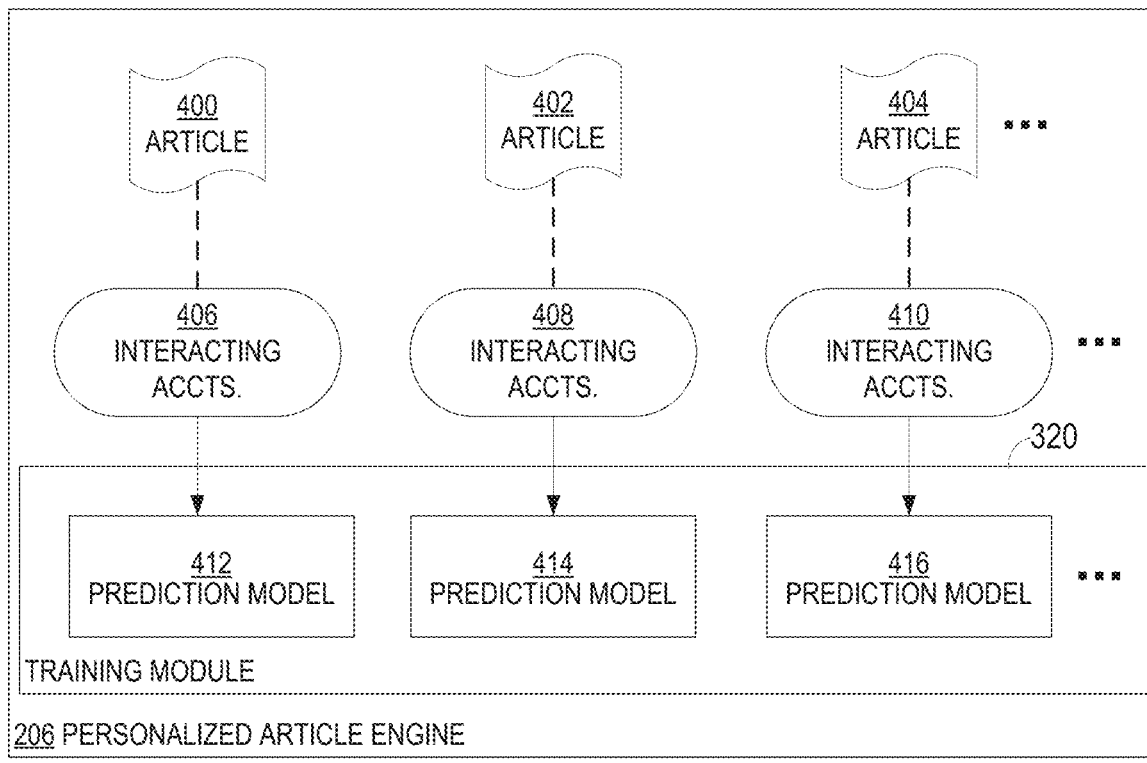
FIG. 4 is a block diagram showing example data flow of a Personalized Article Engine, according to some embodiments.

FIG. 4 is a block diagram showing example data flow of a Personalized Article Engine, according to some embodiments. The data flow may be implemented by one or more of the modules illustrated in FIG. 3, and is discussed by way of reference thereto.

The Personalized Article Engine 206 has access to a plurality of candidate articles 400, 402, 404 in a social network service. It is understood that there can be hundreds, thousands or even millions of candidate articles in the social network service to which the Personalized Article Engine 206 has access. The Personalized Article Engine 206 further has access to profile data of one or more member accounts 406, 408, 410 that have already interacted with each of the articles 400, 402, 404. For example, hundreds of member accounts have interacted with the articles 400, 402, 404. It is understood some member accounts have interacted with all the articles 400, 402, 404, whereas some of the member accounts may have only interacted with some or one of the articles 400, 402, 404.

The training module 320 of the Personalized Article Engine 206 accesses the profile data of the member accounts 406, 408, 410 to train a prediction model 412, 414, 416 for each article 400, 402, 404. That is, a first article 400 has a corresponding first prediction model 412, a second article 402 has a corresponding second prediction model 414, a third article 404 has a corresponding third prediction model 416. The training module 320 may use any one of various known prediction modelling techniques to perform a prediction modelling process to build and train each prediction model 412, 414, 416. Each prediction model 412, 414, 416 returns a score for each corresponding article 400, 402, 404. Each respective score representing a relevance of an article to a target member account. Such relevance of an article can be indicative of a probability of whether the target member account will access the article given the profile data of the member accounts how have already accessed the article.

According to various exemplary embodiments, the training module 320 may perform the prediction modelling process based on a statistics-based machine learning model such as a logistic regression model. As understood by those skilled in the art, logistic regression is an example of a statistics-based machine learning technique that uses a logistic function. The logistic function is based on a variable, referred to as a logit. The logit is defined in terms of a set of regression coefficients of corresponding independent predictor variables. Logistic regression can be used to predict the probability of occurrence of an event given a set of independent/predictor variables. The independent/predictor variables of the logistic regression model are the attributes represented by the assembled feature vectors described throughout. The regression coefficients may be estimated using maximum likelihood or learned through a supervised learning technique from data collected (such as profile data of member account 406, 408, 410) in logs or calculated from log data, as described in more detail below. Accordingly, once the appropriate regression coefficients (e.g., B) are determined, the features included in the assembled feature vector may be input to the logistic regression model in order to predict the probability that the event Y occurs (where the event Y may be, for example, whether a target member account would select to view a particular article).

In other words, provided an assembled feature vector including various features associated with a particular member account, a particular content item, a particular context, and so on, the assembled feature vector may be applied to a logistic regression model to determine the probability that the particular member account will respond to the particular content item in a particular way (e.g., receipt of a mouse click, a request to access, a user selection) given the particular context. Logistic regression is well understood by those skilled in the art, and will not be described in further detail herein, in order to avoid occluding various aspects of this disclosure.

It is understood that the training module 320 may use various other prediction modelling techniques understood by those skilled in the art to predict whether a particular member account will click on a particular content item in a particular context. For example, other prediction modelling techniques may include other machine learning models such as a Naïve Bayes model, a support vector machines (SVM) model, a decision trees model, and a neural network model, all of which are understood by those skilled in the art. Also, according to various exemplary embodiments, the training module 320 may be used for the purposes of both off-line training (for generating, training, and refining a prediction model 412, 414, 416) and online inferences (for predicting whether a particular member will click on a particular content item given a particular context, based on a prediction model that corresponds with the particular content item).

Figure 5:
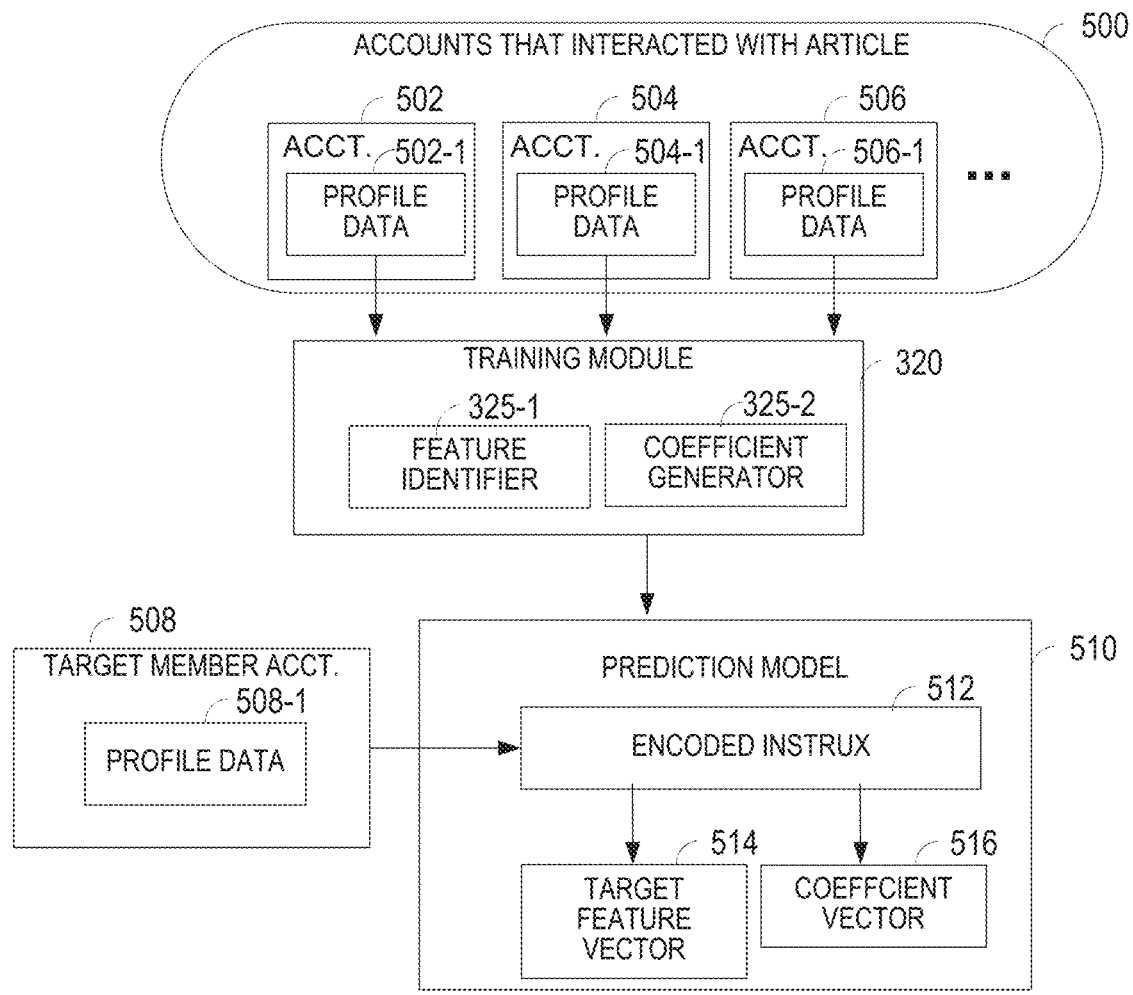
FIG. 5 is a block diagram showing example data flow of a Personalized Article Engine, according to some embodiments.

FIG. 5 is a block diagram showing example data flow of a Personalized Article Engine, according to some embodiments. The data flow may be implemented by one or more of the modules illustrated in FIG. 3 and is discussed by way of reference thereto.

The Personalized Article Engine 206 accesses a plurality of accounts that have interacted with a particular article 500. Each account 502, 504, 506 has corresponding profile data 502-1, 504-1, 506-1. The training module 320 of the Personalized Article Engine 206 executes a logistic regression modelling process with respect to the profile data 502-1, 504-1, 506-1. A feature identifier 325-1 identifies the features of the prediction model 510 for the particular article. It is understood that each feature is based on one or more type(s) of attribute of profile data 502-1, 504-1, 506-1 that is statistically significant in determining whether a given member account will want to access the particular article. Such profile data can be, for example, descriptors of: any of a plurality of types of industry, any of a plurality of types of companies, any of a plurality of types of skills, any of a plurality of types of fields of study, any of a plurality of types of levels of professional experience, any of a plurality of types of schools, and/or any of a plurality of types of job titles. A coefficient generator 325-2 calculates a regression coefficient for each of the identified features according to the logistic regression modelling process.

The training module 320 generates encoded instructions 512 representative of the prediction model 510 for the particular article. The Personalized Article Engine 206 assembles vectors according to the encoded instructions, The encoded instructions indicates a vector position for each type of feature. For example, the Personalized Article Engine 206 assembles a coefficient vector 516 based on the regression coefficients. Each regression coefficient is positioned in the coefficient vector 516 at the vector position for its corresponding feature. For example, a first regression coefficient of a first type of feature is placed in the coefficient vector 516 at the first type of feature's assigned vector position. A second regression coefficient of a second type of feature is placed in the coefficient vector 516 at the second type of feature's assigned vector position.

The Personalized Article Engine 206 assembles a target feature vector 514 based on the profile data 508-1 of a target member account 508. For example, if the first type of feature is present in the profile data 508-1, then a first value is placed in the target feature vector 514 at the first type of feature's assigned vector position. The first value can be a "1" to represent presence of the first type of feature in the profile data 508-1. In other embodiments, the first value can be a pre-defined value for the first type of feature in the profile data 508-1. For example, if the first type of feature corresponds to a geographic region indicator and "San Francisco Bay Area" is pre-assigned a "0.8" value, then "0.8" is placed in the target feature vector 514 at the first type of feature's assigned vector position if the profile data 508-1 of the target member account includes the "San Francisco Bay Area" geographic region indicator. The Personalized Article Engine 206 generates a score based on a dot product of the target feature vector 514 and the coefficient vector 516.

Figure 6:
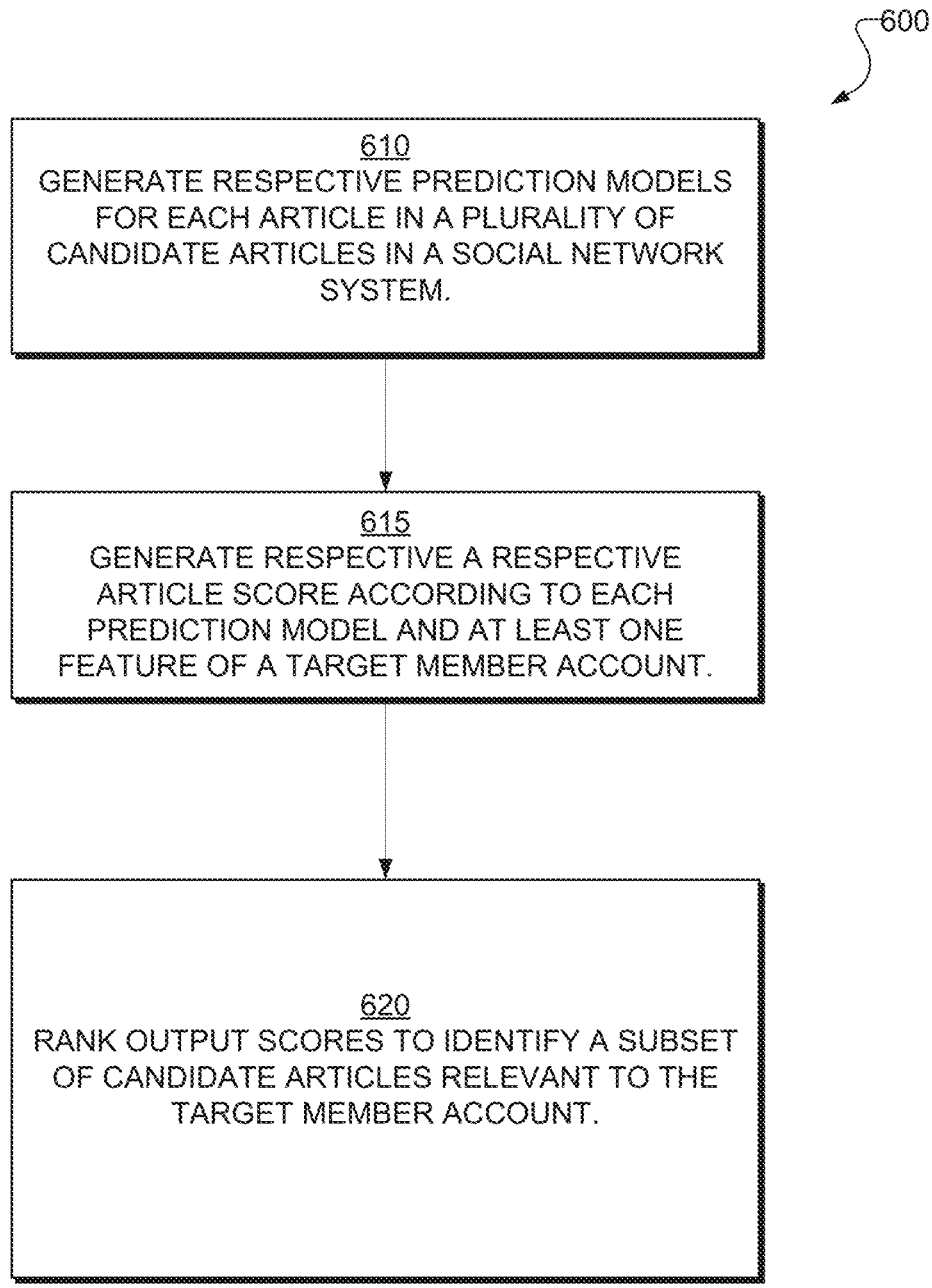
FIG. 6 is a flowchart illustrating an example method for generating a respective score according to a prediction model that corresponds with a particular article according to an example embodiment.

FIG. 6 is a flowchart 600 illustrating an example method for generating a respective score according to a prediction model that corresponds with a particular article according to an example embodiment. The method of FIG. 6 may be implemented by one or more of the modules illustrated in FIG. 3 and is discussed by way of reference thereto.

At operation 610, the Personalized Article Engine 206 generates respective prediction models for each article in a plurality of candidate articles in a social network system.

According to exemplary embodiments, the Personalized Article Engine 206 generates a prediction model for each candidate article from a plurality of candidate articles in a social network system. That is, if there are 100 articles, the Personalized Article Engine 206 trains 100 prediction models, with one prediction model for each candidate article. If there are 1000 candidate articles, the Personalized Article Engine trains 1000 prediction models. A prediction model for a particular candidate article is trained according to the features of the member accounts that have interacted with that particular candidate article. Such features can be, for example, any profile data of those member accounts, such as: industry, company, skills, field of study, experience, school, job title, etc. The Personalized Article Engine 206 generates each respective prediction model by storing features and a coefficients in a data structure that represents the data model (such as a logistic regression model) of the respective prediction model. To execute the respective prediction model, the Personalized Article Engine 206 accesses an instruction set(s) that simulates data model calculations with respect to the features and the coefficients stored in the data structure and profile data of an input member account, such as a target member account.

In one embodiment, each candidate article prediction model is a logistic regression model and will have regression coefficients based on the features of the member accounts that have already interacted with the corresponding candidate article. By training a candidate article prediction model based on the member accounts that have already interacted (e.g. accessed, viewed, shared, liked, commented, posted) with the corresponding candidate article, a more precise determination of relevance of the candidate article can be determined with respect to the features of a target member account—as opposed to relying solely on a generalized prediction model for all candidate articles.

At operation 615, the Personalized Article Engine 206 generates a respective article score according to each prediction model and at least one feature of a target member account.

According to exemplary embodiments, the Personalized Article Engine 206 inputs features of the target member account into each prediction model for each candidate article. For a particular candidate article prediction model, the Personalized Article Engine 206 assembles a vector based on the regression coefficients according to encoded instructions representative of that particular candidate article prediction model. The Personalized Article Engine 206 scores the particular candidate article according to a dot product of the target member account features and the assembled vector. In other words, features of the particular candidate article prediction model's present in the target member account's profile data are detected. A target member account vector is assembled representing the detected features. A coefficient vector is assembled representing each regression coefficient of the particular candidate article prediction. The Personalized Article Engine 206 preforms such scoring according to each respective candidate article model and ranks the candidate articles according to their corresponding scores.

The Personalized Article Engine 206 generates a plurality of output scores based on combining each respective article score with a corresponding article's global model score. At operation 620, the Personalized Article Engine 206 ranks output scores to identify a subset of candidate articles relevant to the target member account.

According to exemplary embodiments, the Personalized Article Engine 206 selects—based on output scores—a subset of the ranked candidate articles, such as the top three candidate articles or the top 25% candidate articles. The Personalized Article Engine 206 includes the selected candidate articles in a message or notification to be sent to the target member account. In various embodiments, the message or notification is generated and sent to the target member account on a daily, weekly or monthly basis. The message or notification informs the target member account of articles that are relevant to the target member account.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 7:
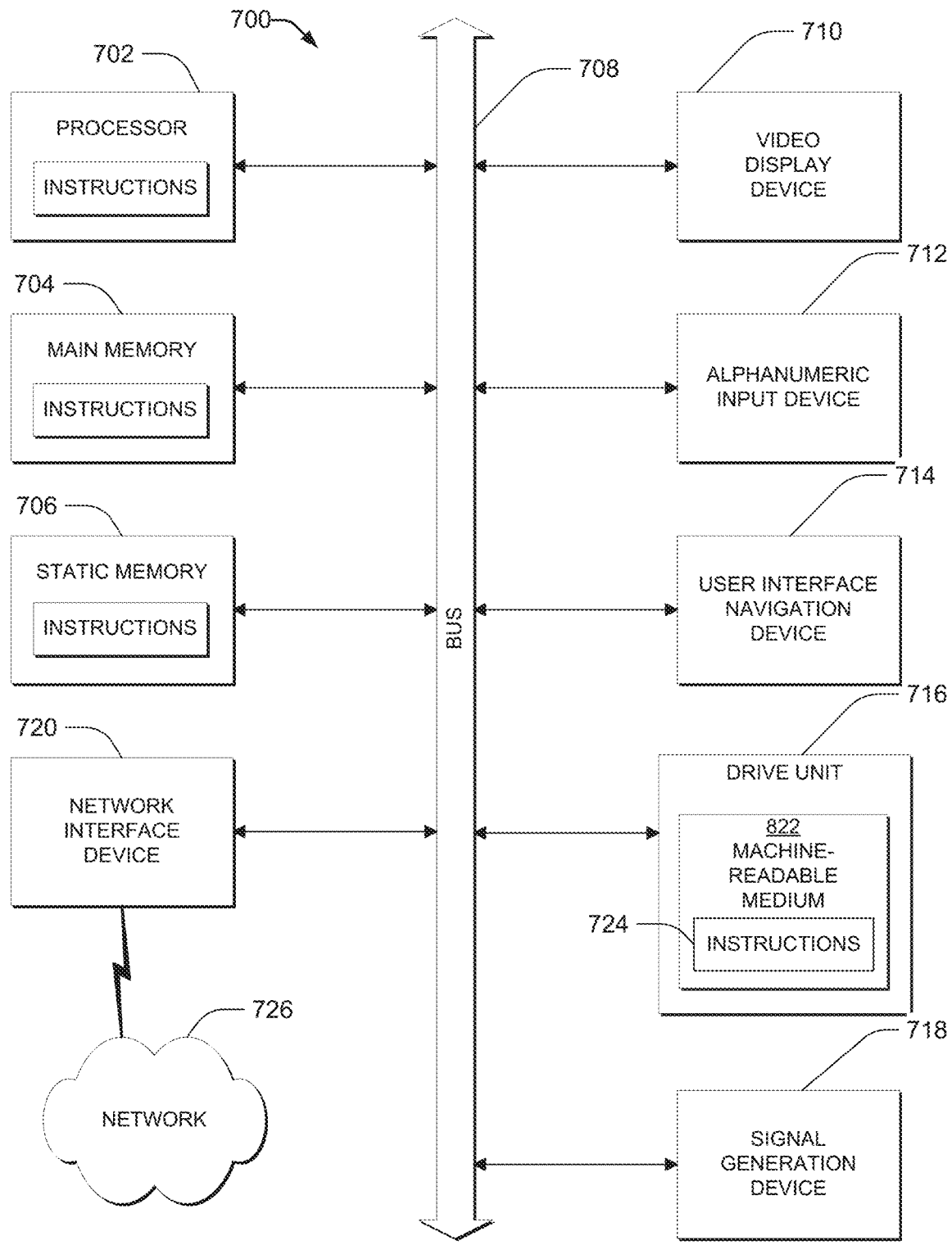
FIG. 7 is a block diagram of an example computer system on which methodologies described herein may be executed, in accordance with an example embodiment.

FIG. 7 is a block diagram of an example computer system 700 on which methodologies described herein may be executed, in accordance with an example embodiment. In alternative embodiments, the machine operates as a stand-alone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 700 includes a processor 702 (e.g., a central processing unit (CPU), a graphics processing unit (GPU) or both), a main memory 704, and a static memory 706, which communicate with each other via a bus 708. Computer system 700 may further include a video display device 710 (e.g., a liquid crystal display (LCD) or a cathode ray tube (CRT)). Computer system 700 also includes an alphanumeric input device 712 (e.g., a keyboard), a user interface (UI) navigation device 714 (e.g., a mouse or touch sensitive display), a disk drive unit 716, a signal generation device 718 (e.g., a speaker) and a network interface device 720.

Disk drive unit 716 includes a machine-readable medium 722 on which is stored one or more sets of instructions and data structures (e.g., software) 724 embodying or utilized by any one or more of the methodologies or functions described herein. Instructions 724 may also reside, completely or at least partially, within main memory 704, within static memory 706, and/or within processor 702 during execution thereof by computer system 700, main memory 704 and processor 702 also constituting machine-readable media.

While machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present technology, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Instructions 724 may further be transmitted or received over a communications network 726 using a transmission medium. Instructions 724 may be transmitted using network interface device 720 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMAX networks). The term "transmission medium" shall be taken to include any intangible medium that is capable of storing, encoding or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the technology. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer system, comprising:
   a processor;
   a memory device holding at least one instruction set executable on the processor to cause the computer system to perform operations comprising:
   generating a different respective per-article prediction model for each article in a plurality of candidate articles in an online network, each different respective per-article prediction model trained, using only profile features from users who interacted with the respective article but not using features associated with the respective article or information about interactions with the respective article, to output a first score indicative of a likelihood that a user will interact with the respective article via a graphical user interface, based on one or more features associated with the user, the training including learning a coefficient for each of the profile features from users who interacted with the respective article;
   generating a global prediction model, the global prediction model trained using a plurality of profile features from users and a plurality of article features to output a second score indicative of a likelihood that an input user will interact with a candidate article via the graphical user interface;
   for each of the plurality of candidate articles and a first user in the online network:
   passing one or more features associated with the first user to the respective per-article prediction model corresponding to the candidate article to output a value for the first score by applying one or more of the learned coefficients to the one or more features associated with the first user, wherein the one or more features associated with the first user are features explicitly provided by the first user in a member profile of the first user;
   passing the one or more features associated with the first user and one or more features associated with the candidate article to the global prediction model to output a value for the second score; and
   combining the value for the first score and the value for the second score to obtain a combined prediction score for the combination of the first user and the candidate article; and
   ranking the candidate articles in the plurality of candidate articles by their respective combined prediction scores.

2. The computer system as in claim 1, wherein generating a different prediction model for each article in the plurality of candidate articles in the online network comprises:
   training a first prediction model for a first article from the plurality of candidate articles in the social network system based on a plurality of features of each member account that has interacted with the first article in the social network system; and
   training a second prediction model for a second article from the plurality of candidate articles based on a plurality of features of each member account that has interacted with the second article in the social network system.

3. The computer system of claim 2, wherein a member account that has interacted with a respective candidate article comprises a member account that has performed any of the following member account actions in the online network: access the respective candidate article, like the respective candidate article, post a comment on the respective candidate article, share the respective candidate article, and post the respective candidate article.

4. The computer system of claim 2, wherein each feature of a respective member account is based on at least any one of the following types of member account profile data: one or more industry descriptors, one or more job title descriptors, one or more employer company descriptors, one or more educational institution descriptors, one or more field of study descriptors, one or more geographic area descriptors and one or more professional level of experience indicators.

5. The computer system of claim 2,
   wherein the first model is a logistic regression model.

6. The computer system of claim 5, wherein the global prediction model is a logistic regression model.

7. The computer system of claim 1, wherein each respective per-article prediction model is stored in a prediction model database.

8. The computer system of claim 1, wherein the features from users who interacted with the respective article include education.

9. The computer system of claim 1, wherein the features from users who interacted with the respective article include skills.

10. The computer system of claim 1, wherein the features from users who interacted with the respective article include location.

11. A non-transitory computer-readable medium storing executable instructions thereon, which, when executed by a processor, cause the processor to perform operations including:
    generating a different respective per-article prediction model for each article in a plurality of candidate articles in an online network, each different respective per-article prediction model trained, using only profile features from users who interacted with the respective article but not using features associated with the respective article or information about interactions with the respective article, to output a first score indicative of a likelihood that a user will interact with the respective article via a graphical user interface, based on one or more features associated with the user, the training including learning a coefficient for each of the profile features from users who interacted with the respective article;
    generating a global prediction model, the global prediction model trained using a plurality of profile features from users and a plurality of article features to output a second score indicative of a likelihood that an input user will interact with a candidate article via the graphical user interface;

for each of the plurality of candidate articles and a first user in the online network:
  passing one or more features associated with the first user to the respective per-article prediction model corresponding to the candidate article to output a value for the first score by applying one or more of the learned coefficients to the one or more features associated with the first user, wherein the one or more features associated with the first user are features explicitly provided by the first user in a member profile of the first user;
  passing the one or more features associated with the first user and one or more features associated with the candidate article to the global prediction model to output a value for the second score; and
  combining the value for the first score and the value for the second score to obtain a combined prediction score for the combination of the first user and the candidate article; and
  ranking the candidate articles in the plurality of candidate articles by their respective combined prediction scores.

12. The non-transitory computer-readable medium as in claim 11, wherein generating a different respective prediction model for each article in the plurality of candidate articles in the online network comprises training a first prediction model for a first article from the plurality of candidate articles in the social network system based on a plurality of features of each member account that has interacted with the first article in the social network system; and
  training a second prediction model for a second article from the plurality of candidate articles based on a plurality of features of each member account that has interacted with the second article in the social network system.

13. The non-transitory computer-readable medium of claim 12, wherein a member account that has interacted with a respective candidate article comprises a member account that has performed any of the following member account actions in the online network: access the respective candidate article, like the respective candidate article, post a comment on the respective candidate article, share the respective candidate article, and post the respective candidate article.

14. The non-transitory computer-readable medium of claim 12, wherein each feature of a respective member account is based on at least any one of the following types of member account profile data: one or more industry descriptors, one or more job title descriptors, one or more employer company descriptors, one or more educational institution descriptors, one or more field of study descriptors, one or more geographic area descriptors and one or more professional level of experience indicators.

15. The non-transitory computer-readable medium of claim 12 wherein the first model is a logistic regression model.

16. The non-transitory computer-readable medium of claim 15, wherein the global prediction model is a logistic regression model.

17. The non-transitory computer-readable medium of claim 11, wherein each respective per-article prediction model is stored in a prediction model database.

18. A method comprising:
  generating a different respective per-article prediction model for each article in a plurality of candidate articles in an online network, each different respective per-article prediction model trained, using only profile features from users who interacted with the respective article but not using features associated with the respective article or information about interactions with the respective article, to output a first score indicative of a likelihood that a user will interact with the respective article via a graphical user interface, based on one or more features associated with the user, the training including learning a coefficient for each of the profile features from users who interacted with the respective article;
  generating a global prediction model, the global prediction model trained using a plurality of profile features from users and a plurality of article features to output a second score indicative of a likelihood that an input user will interact with a candidate article via the graphical user interface;
  for each of the plurality of candidate articles and a first user in the online network:
    passing one or more features associated with the first user to the respective per-article prediction model corresponding to the candidate article to output a value for the first score by applying one or more of the learned coefficients to the one or more features associated with the first user, wherein the one or more features associated with the first user are features explicitly provided by the first user in a member profile of the first user;
    passing the one or more features associated with the first user and one or more features associated with the candidate article to the global prediction model to output a value for the second score; and
    combining the value for the first score and the value for the second score to obtain a combined prediction score for the combination of the first user and the candidate article; and
  ranking the candidate articles in the plurality of candidate articles by their respective combined prediction scores.

19. The method as in claim 18, wherein generating a different respective prediction model for each article in the plurality of candidate articles in the online network comprises:
  training a first prediction model for a first article from the plurality of candidate articles in the social network system based on a plurality of features of each member account that has interacted with the first article in the social network system; and
  training a second prediction model for a second article from the plurality of candidate articles based on a plurality of features of each member account that has interacted with the second article in the social network system.

20. The method of claim 19, wherein a member account that has interacted with a respective candidate article comprises a member account that has performed any of the following member account actions in the online network: access the respective candidate article, like the respective candidate article, post a comment on the respective candidate article, share the respective candidate article, and post the respective candidate article.

21. The method of claim 19, wherein each feature of a respective member account is based on at least any one of the following types of member account profile data: one or more industry descriptors, one or more job title descriptors, one or more employer company descriptors, one or more educational institution descriptors, one or more field of study descriptors, one or more geographic area descriptors and one or more professional level of experience indicators.

22. The method of claim 19, wherein the first model is a logistic regression model.

23. The method of claim 22, wherein the global prediction model is a logistic regression model.

* * * * *